(12) United States Patent
Gopalakrishnakone et al.

(10) Patent No.: US 6,613,745 B1
(45) Date of Patent: Sep. 2, 2003

(54) THERAPEUTIC MOLECULES DERIVED FROM SNAKE VENOM

(75) Inventors: Ponnampalam Gopalakrishnakone, Singapore (SG); Xiao Chun Pu, Montreal (CA); Peter Tsun-Hon Wong, Singapore (SG); Mathew Choon Eng Gwee, Singapore (SG); R. Manjunatha Kini, Singapore (SG)

(73) Assignee: National University of Singapore (SG)

( * ) Notice: Subject to any disclaimer, the term of this patent is extended or adjusted under 35 U.S.C. 154(b) by 0 days.

(21) Appl. No.: 09/530,799

(22) PCT Filed: Nov. 3, 1998

(86) PCT No.: PCT/SG98/00087

§ 371 (c)(1), (2), (4) Date: Jul. 26, 2000

(87) PCT Pub. No.: WO99/24055

PCT Pub. Date: May 20, 1999

(30) Foreign Application Priority Data

Nov. 6, 1997 (SG) ............................................. 9703972

(51) Int. Cl.[7] ........................ A61K 38/00; A61K 38/04; C07K 7/00
(52) U.S. Cl. .......................... 514/15; 514/17; 530/327; 530/328; 530/330; 530/334; 530/344; 536/23.5; 435/69.1; 435/252.3; 435/320.1
(58) Field of Search ..................... 514/15, 17; 530/327, 530/334, 328, 344, 330; 536/23.51; 435/69.1, 252.3, 320.1

(56) References Cited

FOREIGN PATENT DOCUMENTS

DE        A2130708        12/1971
WO        A1-9208472      5/1992

OTHER PUBLICATIONS

Joubert, Biochem. Biophys. Acta 317, 85–98 (1973).*
Chang et al., Sequence characterization of a novel a–neurotoxin from the king cobra (Ophiophagus hannah) venom. Biochem. Biohys. Res. Comm. 191, 214–223 (Feb. 1993).*
Song, et al., Purification, sequence and pharmaceutical studies of a new alpha–neurotoxin from Ophiophagus hannah venom. Toxicon 32, 537–538 (1994) abstract.*
Pu et al., A novel analgesic toxin (Hannalgesin) from the venom of king cobra (Ophiophagus hannah). Toxicon 33, 1425–1431 (1995).*
Database WPI on Questel, JP 57–116 019 A Jul. 19, 1982, English Abstract only.
Database WPI on Questel, CN 1 088 832 A Jul. 6, 1994, English Abstract only.
Dateabase WPI on Questel, CN 1 102 570 A May 17, 1995, English Abstract only.

* cited by examiner

Primary Examiner—Christopher S. F. Low
Assistant Examiner—Chih Min Kam
(74) Attorney, Agent, or Firm—Birch, Stewart, Kolasch & Birch, LLP

(57) ABSTRACT

The present invention relates generally to peptide molecules and to derivatives, homologues, analogues and mimetics thereof capable of inducing or facilitating analgesia or partial analgesia alone or in combination with other analgesic molecules. The present invention also contemplates a method of inducing or facilitating analgesia or partial analgesia by the administration of a peptide or a derivative, homologue, analogue or mimetic thereof. The amino acid sequence of the peptide molecules of the present invention are derived from or based on amino acid sequences of snake venom toxins, and, in particular, α-neurotoxins.

30 Claims, 3 Drawing Sheets

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Derived from the venom of various families of
      snakes

<400> SEQUENCE: 1

Asn Pro Phe Pro Thr
1               5

<210> SEQ ID NO 2
<211> LENGTH: 11
<212> TYPE: PRT
<213> ORGANISM: Artificial Sequence
<220> FEATURE:
<223> OTHER INFORMATION: Derived from the venom of various families of
      snakes
<221> NAME/KEY: misc_feature
<222> LOCATION: (6)..(6)
<223> OTHER INFORMATION: Xaa equals any amino acid
<221> NAME/KEY: misc_feature
<222> LOCATION: (7)..(7)
<223> OTHER INFORMATION: Xaa equals any amino acid
<221> NAME/KEY: misc_feature
<222> LOCATION: (10)..(10)
<223> OTHER INFORMATION: Xaa equals any amino acid
<221> NAME/KEY: misc_feature
<222> LOCATION: (11)..(11)
<223> OTHER INFORMATION: Xaa equals any amino acid

<400> SEQUENCE: 2

Asn Pro Phe Pro Thr Xaa Xaa Lys Arg Xaa Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Derived from the venom of various families of
      snakes

<400> SEQUENCE: 3

Asn Pro Phe Pro Thr Trp Arg Lys Arg Pro Gly
1               5                   10
```

```
<210> SEQ ID NO 4
<211> LENGTH: 9
<212> TYPE: PRT
<213> ORGANISM: Artificial Sequence
<220> FEATURE:
<223> OTHER INFORMATION: Derived from the venom of various families of
      snakes

<400> SEQUENCE: 4

Asn Pro Phe Pro Thr Arg Lys Arg Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Derived from the venom of various families of
      snakes

<400> SEQUENCE: 5

Asn Pro Phe Pro Thr Trp Arg Lys Arg Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Derived from the venom of various families of
      snakes

<400> SEQUENCE: 6

Asn Pro Phe Pro Thr Trp Lys Arg Lys His
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Derived from the venom of various families of
      snakes

<400> SEQUENCE: 7

Asn Pro Phe Pro
1

<210> SEQ ID NO 8
<211> LENGTH: 9
<212> TYPE: PRT
<213> ORGANISM: Artificial Sequence
<220> FEATURE:
<223> OTHER INFORMATION: Derived from the venom of various families of
      snakes

<400> SEQUENCE: 8

Asn Pro Phe Pro Thr Trp Lys Arg Lys
1               5

<210> SEQ ID NO 9
<211> LENGTH: 6
<212> TYPE: PRT
<213> ORGANISM: Ophiohagus hannah
<220> FEATURE:
<221> NAME/KEY: misc_feature
<222> LOCATION: (4)..(4)
<223> OTHER INFORMATION: Xaa is Thr or Arg
<221> NAME/KEY: misc_feature
```

-continued

```
<222> LOCATION: (5)..(5)
<223> OTHER INFORMATION: Xaa is Asp or Thr
<221> NAME/KEY: misc_feature
<222> LOCATION: (6)..(6)
<223> OTHER INFORMATION: Xaa is Asn or Lys

<400> SEQUENCE: 9

Cys Cys Ser Xaa Xaa Xaa
1               5
```

THERAPEUTIC MOLECULES DERIVED FROM SNAKE VENOM

This application is the national phase under 35 U.S.C. §371 of PCT International Application No. PCT/SG98/00087 which has an International filing date of Nov. 3, 1998, which designated the United States of America.

FIELD OF THE INVENTION

The present invention relates generally to peptide molecules and to derivatives, homologues, analogues and mimetics thereof capable of inducing or facilitating analgesia or partial analgesia alone or in combination with other analgesic molecules. The present invention also contemplates a method of inducing or facilitating analgesia or partial analgesia by the administration of a peptide or a derivative, homologue, analogue or mimetic thereof. The amino acid sequence of the peptide molecules of the present invention are derived from or based on amino acid sequences of snake venom toxins, and, in particular, α-neurotoxins.

BACKGROUND OF THE INVENTION

The increasing demand for improved and more efficacious analgesics is providing the incentive for the pharmaceutical industry to consider new approaches for identifying and designing new therapeutic molecules. One source considered to be of potential interest in the quest for new pharmaceutical agents is the identification of molecules from the natural environment including molecules from life forms in the environment. Much effort is now being spent, therefore, on screening aquatic environments, river beds, coral, plants, microorganisms and higher animals for potentially useful molecules. This search is often referred to as "natural product screening". The level of biodiversity in the Asian and Australasian regions provides a particularly useful target for natural product screening.

Reptiles are one of the oldest life forms on earth of which snakes form a particularly interesting group. Many venomous snakes have evolved toxin molecules such as α-neurotoxins which are highly effective in inducing a range of neurological dysfunctions.

Whereas snake venom has been studied to the extent of producing antidotes and antivenene, snakes have not been extensively studied as a potential source of therapeutic molecules.

In work leading up to the present invention, the inventors studied snake venom from a particularly venomous snake, the King cobra (*Ophiophagus hannah*). This snake is broadly distributed in India, Burma, Thailand, Malaysia, Indochina, Southern China, Indonesia, Japan and the Philippines (Tin et al, 1991). To date, six α-neurotoxins have been isolated from the king cobra venom (Joubert, 1973; Chang et al, 1993; Song et al, 1994). Little, however, is known of the pharmacological properties of those toxins.

The inventors have now surprisingly determined that peptide molecules having an amino acid sequence or derived from or based on portions of snake venom toxins have analgesic properties.

SUMMARY OF THE INVENTION

One aspect of the present invention provides a peptide comprising a sequence of amino acids having at least 60% similarity to a sequence of amino acids from a portion of a toxin from snake venom and which peptide is capable of inducing or facilitating analgesia or a derivative, homologue, analogue or mimetic of said peptide.

Another aspect of the present invention relates to a peptide comprising a sequence of amino acids having at least 60% similarity to an amino acid sequence from a portion of an α-neurotoxin from venom from a snake of the family of snakes selected from Elapidae, Viperidae, Colubridae or Crotalidae and which peptide is capable of inducing or facilitating analgesia or a derivative, homologue, analogue or mimetic of said peptide.

Yet another aspect of the present invention is directed to a peptide comprising the amino acid sequence N P F P T (SEQ ID NO:1) and which peptide is capable of inducing or facilitating analgesia or a derivative, homologue, analogue or mimetic of said peptide.

Still yet another aspect of the present invention provides a peptide having the amino acid sequence N P F P T $X_1$ $X_2$ K R $X_3$ $X_4$ (SEQ ID NO:2) wherein $X_1$, $X_2$, $X_3$, $X_4$ may be the same or different and each is any amino acid residue wherein said peptide is capable of inducing of facilitating analgesia or a derivative, homologue, analogue or mimetic of said peptide.

In yet another aspect of the present invention, there is provided a peptide having an amino acid sequence selected from the list consisting of:

N P F P T W R K R P G (SEQ ID NO:3);
N P F PT R K R P (SEQ ID NO:4);
N P F P T W R K R P (SEQ ID NO:5); and
N P F P T W K R K H (SEQ ID NO:6);

or a derivative, homologue, analogue or mimetic of one or more of SEQ ID NO:3, SEQ ID NO:4, SEQ ID NO:5 or SEQ ID NO:6 and wherein said peptide is capable of inducing or facilitating analgesia.

The present invention also provides a composition comprising a peptide as defined above alone or in combination with one or more pharmaceutically acceptable carriers and/or diluents and/or one or more other active molecules such as an analgesic molecule or compound.

Still another aspect of the present invention contemplates a method of inducing or facilitating analgesia said method comprising administering a peptide as hereinbefore defined for a time and under conditions sufficient to induce pain relief.

Even yet another aspect of the present invention is directed to the use of a peptide as hereinbefore defined in the manufacture of a medicament for inducing or facilitating analgesia.

The present invention further extends to antibodies to the peptides as hereinbefore defined.

The peptides of the present invention are referred to as "analgesic" peptides.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Bibliographic details of the publications referred to by author in this specification are collected at the end of the description.

Sequence Identity Numbers (SEQ ID NOs.) for the amino acid sequences referred to in the specification are defined following the bibliography.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

DETAILED DESCRIPTION OF THE INVENTION

Figure 1:
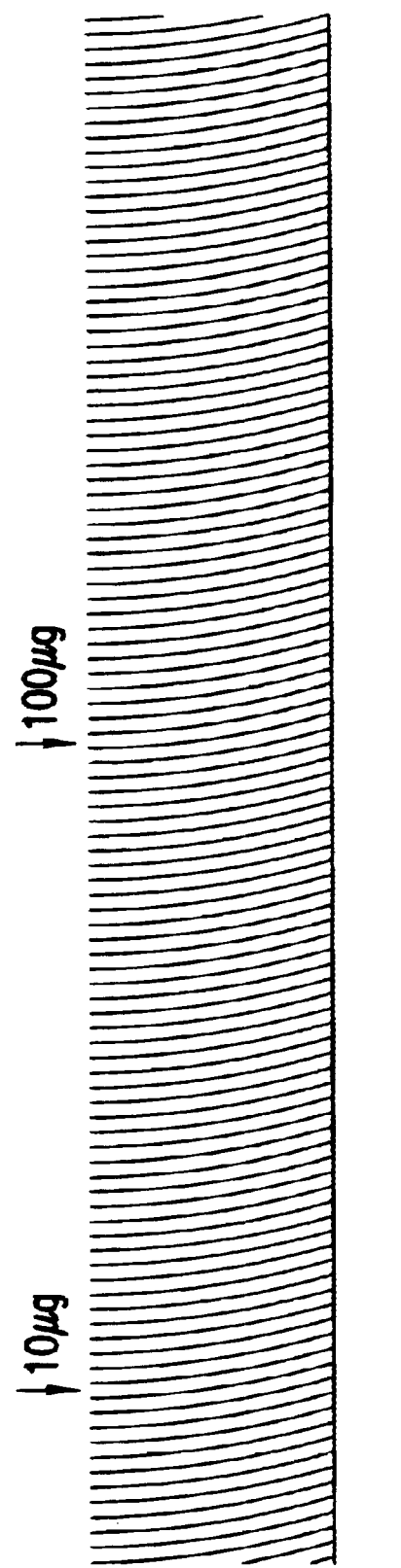
FIG. 1 is graphical representation of typical tracings showing that the addition of 10 μg of analgesic peptide had no effect on the contractile (twitch) responses of the chick biventer muscle evoked by electrical field stimulation (25 V, 5 Hz×10s, 1 ms pulse width, every 100s).

The present invention provides a peptide or a derivative, homologue, analogue or mimetic thereof which comprises an amino acid sequence which is at least 60% similar to a sequence of amino acids in a toxin and, more particularly, an α-neurotoxin from snake venom and which peptide is capable of inducing or facilitating analgesia. The peptide is conveniently, in isolated or purified form.

The term "analgesia" is used in its broadest sense to include any form of pain relief ranging from complete removal of pain to a reduced level of pain. The pain relief may be considered a reduced sensibility to pain without loss of consciousness. The pain relief may be localized or systemic. Pain includes acute pain, sharp localised pain, more centralized pain and any other form of sensation which contributes to discomfort. An "analgesic" is considered herein to be a molecule which induces analgesia.

The subject of the analgesia is generally a warm blooded animal or bird such as but not limited to a human, primate, livestock animal (eg. sheep, cow, horse, donkey, pig), companion animal (eg. dog, cat), laboratory test animal (eg. mouse, rat, guinea pig, rabbit, hamster), captive wild animal (eg. deer, fox), caged bird (eg. parrot) and poultry bird (eg. chicken, duck, pheasant, goose, turkey). Preferably, the subject is a human, primate or other warm blooded mammal. Most preferably, the subject is a human.

The term "peptide" encompasses a proteinaceous molecule comprising from about 2 amino acid residues to about 50 amino acid residues. Preferably, the peptide comprises from about 3 amino acid residues to about 40 amino acid residues. Even more preferably, the peptide comprises from about 4 amino acid residues to about 30 amino acid residues. Particularly preferred embodiments include peptides comprising from about 4 amino acid residues to about 20 amino acid residues such as from 4 to 15 and 4 to 10 amino acid residues. Although the amino acid sequence of the analgesic peptides is derived from or based on an (α-neurotoxin from snake venom, it does not extend to the full length α-neurotoxin but rather only to a part thereof.

The analgesic peptide may be glycosylated or unglycosylated and/or may contain a range of other molecules fused, linked, bound or otherwise associated to the peptide such as amino acids, lipids, carbohydrates or other peptides, polypeptides or proteins. Reference hereinafter to a "peptide" includes a peptide comprising a sequence of amino acids as well as a peptide associated with other molecules such as amino acids, lipids, carbohydrates or other peptides, polypeptides or proteins. For the purposes of the present description, a molecule comprising a sequence of at least about 50 amino acids is regarded as a peptide.

The analgesic peptides of the present invention may be produced by chemical synthetic techniques or may be produced by recombinant DNA technology as discussed further below. The peptides may also be fragments of larger x-neurotoxin molecules from snake venom. The fragments may be naturally occurring fragments or generated by the action of proteases, peptidases, amidases, lysins or other enzymes as well as by sonic disruption, heat, chemical disruption and/or shearing.

The amino acid sequence of the analgesic peptides of the present invention are considered to be derived from or based on a snake venom toxin and, more particularly, α-neurotoxin. This is not to imply, however, that the preferred peptides are necessarily derivatives of naturally occurring snake venom toxins since particularly useful peptides are, in accordance with the present invention, chemically synthesised based on the amino acid sequence of a larger snake venom toxin.

Preferred snakes include snakes from the family Colubridae, Elapidae, Viperidae and Crotalidae such as species of the genera Naja, Dendroaspis, Bungarus, Pseudechis, Ophiophagus and Hemachatus. Particularly preferred snakes are from the family Elapidae such as but not limited to King cobra (*Ophiohagus hannah*); True cobras (Naja spp); Asian or Indian cobra (*N. naja*); Egyptian cobra (*N. haje*); Spitting cobra (*N. nigricolli*); Black-lipped cobra (*N. malenoleuca*); Cape cobra (*N. nivea*); Gold's tree cobra (*Pseudohaje goldii*); Desert black snakes (Walterinnesia spp); Shield-nose snakes (Aspidelaps spp); Water cobras or water snakes (Boulengerina spp); Black mamba (*Dendroaspis polylepis*); Mamba (*D. angusticeps*); Kraits snake (Bungarus spp); Oriental coral snakes (Calliophis spp); Long-glanded coral snakes (Maticora spp); American coral snakes (Micurus spp); Southern coral snake (*M. frontalis*); Eastern coral snake or Harlequin snake (*M. fulvius*); Western coral snake (Micruroides spp); Arizona coral snake (*M. euryxanthus*); Death adder (*Acanthophis antarcticus*); Australian tiger snakes (Notechis spp); and Australian copperhead (Denisomia spp).

The present invention is exemplified with respect to peptides based on snake venom toxins from *O. hannah* and is particularly exemplified from *O. hannah* venom α-neurotoxins referred to as toxin a, toxin b and toxin (CM-11 (Joubert, 1973; Change et al, 1993; Song et al, 1994; Pu et al, 1995). However, the present invention extends to any toxin and more particularly α-neurotoxin from the venom of *O. hannah* as well as from the venom of any other snake such as from the family Elapidae or the families of Colubridae, Viperidae and Crotalidae.

According to a particularly preferred embodiment of the present invention, there is provided a peptide comprising a sequence of amino acids of from about 2 to about 50 residues having at least about 60% similarity to a sequence of amino acids from a α-neurotoxin isolatable from snake venom from a snake within the family Elapidae wherein said peptide is capable of inducing or facilitating analgesia in a mammal or a derivative, homologue, analogue or mimetic of said peptide.

More particularly, the present invention contemplates a peptide comprising from about four to about 30 amino acid residues wherein all or a portion of the sequence has at least about 60% similarity to an α-neurotoxin from *O. hannah* snake venom and wherein said peptide induces or facilitates analgesia in a mammal.

The percentage similarity may be greater than 60% such as at least about 70% or at least about 80% or at least about 90% or higher.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

Preferred a-neurotoxins from *O. hannah* include toxin a, toxin b and CM-11 amongst other α-neurotoxins such as those having an N-terminal amino acid sequence which includes the amino acid sequence C C S $X_a$ $X_b$ $X_c$ (SEQ ID NO:9) wherein $X_a$ is T or R;
$X_b$ is D or T; and
$X_c$ is N or K.

One particularly useful group of peptides of the present invention have analgesic properties inhibited by naloxone and $N^w$-nitro-L-arginine methyl ester (L-NAME). Although in no way intending to limit the present invention to any one theory or mode of action, this implies the involvement of the opioid and nitric oxide systems, respectively.

Accordingly, another preferred embodiment of the present invention provides a peptide having the following characteristics:

(i) induces or facilitates analgesia in a mammal;
(ii) comprises from about 2 to about 50 amino acid residues;
(iii) its analgesic ability is capable of inhibition by naloxone and or L-NAME; and
(iv) comprises an amino acid sequence of which at least four amino acid residues are common to the amino acid sequence of an α-neurotoxin from *O. hannah;* or a derivative, homologue, analogue or mimetic of said peptide.

A particularly preferred peptide of the present invention comprises the amino acid sequence N P F P T (SEQ ID NO:1) and even more preferably the amino acid sequence N P F P T $X_1$ $X_2$ K R $X_3$ $X_4$ (SEQ ID NO:2) wherein $X_1$, $X_2$, $X_3$ and $X_4$ may be the same or different and each is an amino acid residue. Preferably, $X_1$ is absent or is W, $X_2$ is absent or is R, $X_3$ is P or K and $X_4$ is absent or is G or H. Most preferably, the peptide comprises the amino acid sequences:

N P F P T W R K R P G (SEQ ID NO:3);
N P F P T R K R P (SEQ ID NO:4);
N P F PT W R K R P (SEQ ID NO:5); and
N P F P T W K R K H (SEQ ID NO:6);

or derivatives, homologues, analogues or mimetics thereof.

Reference herein to "derivatives" includes parts, fragments and portions of the subject analgesic peptides. A derivative also includes a single or multiple amino acid substitution, deletion and/or addition. Homologues include functionally, structurally or sterochemically similar peptides from venom from the same species of snake or from within the same genus or family of snake. For example, a homologue would include a peptide having, for example, the amino acid sequence N P F P (SEQ ID NO:7) from another a-neurotoxin from another member of the Elapidae family. Alternatively, the amino acids N P F P (SEQ ID NO:7) may be replaced by amino acids having a similar charge, stereochemistry, conformation or peptide conformation influencing ability. All such homologues are contemplated by the present invention.

Analogues and mimetics include molecules which include molecules which contain non-naturally occurring amino acids or which do not contain amino acids but nevertheless behave functionally the same as the peptide. Natural product screening is one useful strategy for identifying analogues and mimetics.

Although, analogues of the subject peptides contemplated herein include modifications to side chains, incorporation of unnatural amino acids and/or their derivatives during peptide synthesis and the use of crosslinkers and other methods which impose conformational constraints on the peptide molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-a-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |

TABLE 2-continued

| Non-conventional amino acid | Code | Non-conventional amino acid | Code |
|---|---|---|---|
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of the subject peptides capable of acting as antagonists or agonists of the analgesic peptides. Chemical analogues may not necessarily be derived from the peptides themselves but may share certain conformational similarities. Alternatively, chemical analogues may be specifically designed to mimic certain physiochemical properties of the peptides. Chemical analogues may be chemically synthesised or may be detected following, for example, natural product screening.

All these types of modifications may be important to stabilise the subject peptide if administered to a subject.

As stated above, the peptides of the present invention are useful in inducing or facilitating analgesia in a subject such as a mammal (eg. a human).

Accordingly, another aspect of the present invention contemplates a method of inducing analgesia in a subject said method comprising administering to said subject a pain alleviating effective amount of a peptide as hereinbefore defined for a time and under conditions sufficient to induce analgesia or to otherwise reduce the level of pain.

Preferably, the peptide administered comprises an amino acid sequence having at least about 60% similarity to an α-neurotoxin from *O. hannah* or is a derivative, homologue, analogue or mimetic thereof.

In accordance with this method, more than one type of peptide may be administered or the peptide may be co-administered with a known analgesic compound or molecule. By “co-administered” is meant simultaneous administration in the same formulation or in two different formulations via the same or different routes or sequential administration by the same or different routes. By “sequential” administration is meant a time difference of from seconds, minutes, hours or days between the administration of the two types of peptides or the peptide and the known analgesic compound or molecule. The peptides or the peptide and known analgesic compound or molecule may be administered in any order.

Routes of administration include but are not limited to intravenously, intraperitioneal, subcutaneously, intracranial, intradermal, intramuscular, intraocular, intrathecal, intracerebrally, intranasally, infusion, orally, rectally, via iv drip, patch and implant. Intravenous and intraperitoneal and anal routes are particularly preferred.

Another aspect of the present invention provides a composition for use inducing or facilitating analgesia comprising a peptide as hereinbefore defined and one or more pharmaceutically acceptable carriers and/or diluents. The composition may also comprise two different types of peptides or a peptide and a known analgesic compound or molecule.

Compositions suitable for injectable use include sterile aqueous solutions (where water soluble) and sterile powders for the extemporaneous preparation of sterile injectable solutions. They must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, the analgesic peptides may need to be modified to permit penetration of the surface barrier.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for induce or facilitating analgesia in living subjects.

Effective amounts of analgesic peptides contemplated by the present invention will vary depending on the severity of the pain and the health and age of the recipient. In general terms, effective amounts may vary from 0.01 ng/kg body weight to about 100 mg/kg body weight. Alternative amounts include for about 0.1 ng/kg body weight about 100 mg/kg body weight or from 1.0 ng/kg body weight to about 80 mg/kg body weight.

Still another aspect of the present invention is directed to antibodies to the subject peptides and their derivatives, homologues, analogues and mimetics. Such antibodies may be monoclonal or polyclonal.

In the case of small peptides, these may first need to be associated with a carrier molecule.

The antibodies of the present invention are particularly useful as therapeutic or diagnostic agents. For example, specific antibodies can be used to screen for peptides using immunoassays or used as antagonists to inhibit peptide activity under certain circumstances such as where temporary analgesia is only required. Techniques for such immunoassays are well known in the art and include, for example, sandwich assays and ELIZA. Knowledge of peptide levels may be important for monitoring certain therapeutic protocols.

Antibodies to the peptides (or their derivatives, homologues, analogues or mimetics) of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies.

As stated above, specific antibodies can be used to screen for the subject peptides. The latter would be important, for example, as a means for screening for levels of peptides in a cell extract or other biological fluid or purifying peptides made by recombinant means from culture supernatant fluid.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of peptide.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of peptide, or antigenic parts thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting a subject peptide in a biological sample from a subject or culture supernatant flow or other source said method comprising contacting said biological sample with an antibody specific for said peptide or its derivative, homologue, analogue or mimetic for a time and under conditions sufficient for an antibody-peptide complex to form, and then detecting said complex.

The presence of a peptide may be accomplished in a number of ways such as by Western blotting and ELISA procedures. A wide range of immunoassay techniques are available as can be seen by reference to U.S. Pat. Nos. 4,016,043, 4, 424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain an analgesic peptide including cell extract, culture supernatant tissue biopsy, serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the peptide or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from room temperature to about 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, luciferase glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. In all cases, the enzyme-labelled antibody is added to the first antibody-peptide complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention further contemplates recombinant analgesic peptides. Accordingly, another aspect of the present invention provides a nucleic acid molecule comprising a sequence of nucleotides encoding or complementary to a sequence encoding a peptide as hereinbefore defined or a derivative or homologue thereof.

A particularly useful nucleic acid molecule is one which encodes or is complementary to a sequence which encodes a peptide amino acid sequence N P F P T (SEQ ID NO:1), said peptide capable of inducing or facilitating analgesia or a derivative or homologue of said peptide.

Even more preferably, the nucleic acid comprises a nucleotide sequence encoding or complementary to a sequence encoding the amino acid sequence N P P P T $X_1$ $X_2$ K R $X_3$ $X_4$ [SEQ ID NO:2]
where $X_1$, $X_2$, $X_3$ and $X_4$ may be the same or different and each is any amino acid residue, said peptide capable of inducing or facilitating analgesia or a derivative or homologue of said peptide.

Still yet more particularly, the nucleic acid molecule comprises a sequence of nucleotides encoding or complementary to a sequence encoding an amino acid sequence selected from:

N P F P T W R K R P G (SEQ ID NO:3);
N P F P T R K R P (SEQ ID NO:4);
N P F P T W R K R P (SEQ ID NO:5); and
N P F P T W K R K H (SEQ ID NO:6).

The nucleic acid molecule of the present invention is generally in isolated form. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptides which forms are encompassed by the present invention.

The present invention further encompasses host cells for the subject nucleic acid molecules and which are used to produce recombinant peptides. The host cells may be prokaryotic cells or eukaryotic cells. Examples of prokaryotic cells include *E. coli*, Bacillus sp, Pseudomonas sp amongst many others. Examples of eukaryotic cells include mammalian cell lines (eg. CHO cells), yeast cells, fungal cells, insect cells, plant cells and reptilian cell lines. The ability to produce recombinant peptides of the present invention permits the large scale production of vast qualities of peptides for commercial uses. As stated above, the peptide may need to be produced as part of a large peptide, polypeptide or protein which may be used as is or may first need to be processed in order to remove the extraneous proteinaceous sequences. Such processing includes digestion with proteases, peptidases and amidases or a range of chemical, electrochemical, sonic or mechanical disruption techniques.

Notwithstanding that the present invention encompasses recombinant peptides, chemically synthetic techniques are particularly preferred in the synthesis of the peptides. The peptide fragments such as those set forth in SEQ ID NO:3 to 6 are conveniently synthesized based on larger toxin molecules isolated from snake venom. Isolation of the larger toxin molecules may be accomplished by any suitable means such as by chromatographic separation, for example using CM-cellulose ion exchange chromatography followed by Sephadex (eg. G-50 column) filtration. Many other techniques are available including HPLC, PAGE amongst others. Once purified, the toxin can be partially sequenced and/or fragments produced and used directly as a source of peptides or as a template for peptide synthesis.

Peptides may be synthesized by solid phase synthesis using F-moc chemistry as described by Carpino et al (1991). The peptide and fragments thereof may also be synthesized by alternative chemistries including, but not limited to, t-Boc chemistry as described in Stewaart et al (1985) or by either classical methods of liquid phase peptide synthesis. The synthesized peptides are conveniently tested for analgesic activity in a hot-plate test (see Examples).

The present invention further extends to the use of the subject peptides in the manufacture of a medicament for inducing or facilitating analgesia.

Preferred peptides are those which comprises the amino acid sequence N P F P T (SEQ ID NO:1), and more preferably the amino acid sequence N P F P T $X_1$ $X_2$ K R $X_3$ $X_4$ (SEQ ID NO:2) wherein $X_1$, $X_2$, $X_3$, $X_4$ may be the same or different and each is any amino acid.

Particularly preferred peptides are selected from:

N P F P T W R K R P G [SEQ ID NO:3];

N P F P T R K R P [SEQ ID NO:4];

N P F PT W R K R P [SEQ ID NO:5]; and

N P F P T W K R K H [SEQ ID NO:6].

Yet another aspect of the present invention provides an agent useful or inducing or facilitating analgesia comprising a peptide as hereinbefore defined.

The present invention is further described by the following non-limiting Examples.

EXAMPLE 1

Animals

Swiss albino mice (female, 18–22 g) were obtained from the University Laboratory Animal Centre, National University of Singapore, Singapore.

EXAMPLE 2

Peptide Synthesis

The peptide fragments

Asn-Pro-Phe-Pro-Thr-Trp-Arg-Lys-Arg-Pro-Gly (SEQ ID NO:3);

Asn-Pro-Phe-Pro-Thr-Arg-Lys-Arg-Pro (SEQ ID NO:4);

Asn-Pro-Phe-Pro-Thr-Trp-Arg-Lys-Arg-Pro (SEQ ID NO:5); and

Asn-Pro-Phe-Pro-Thr-Trp-Lys-Arg-Lys-His (SEQ ID NO:6);

were synthesized based on the 72 amino acid sequence of hannalgesin (Pu et al, 1995) and the corresponding homologous sequences in toxin and toxin b (Joubert, 1973). The first 10 amino acids of peptide -N-P-F-P-T-W-R-K-R-P (SEQ ID NO:5) is homologous or shows a high degree of homology with the terminal portions of the King cobra toxins; the last amino acid, glycine, has no significance as it was part of the synthetic protein fragments used to synthesize the peptide. The peptide was synthesized by solid phase synthesis using F-moc chemistry as described by Carpino. Table 3 provides a comparison of amino acid sequences from the peptide fragment.

The synthesized peptide was tested for analgesic activity in the hot-plate test. The neurotoxic effects was also tested on the chick biventral.

EXAMPLE 3

Chick Biventral Experiment

Local domestic chicks (*Gallus domesticus*) of 5 to ten days old were killed with $CO_2$; the upper oesophagus up to the crop was removed and mounted under 1 g tension in 6 ml Krebs solution, maintained at 32° C. and aerated with 5% v/v $CO_2$ in oxygen.

Electrical field stimulation (EFS:25 V, 5 Hz×10 S, 1 MS pulse width, every 100s) was applied to produce contractile responses of the oesophagi. Responses were recorded on a Grass polygraph via a force displacement transducer (model FT03, Grass). After the contraction of oesophagi reached stability, the synthesized peptide (10 μG) was added to see whether it blocked the contractile response.

As shown in FIG. 1, after adding an analgesic peptide, the contractile response of chick biventer showed no change. Therefore, the peptide had no neurotoxic effect on the neuromuscular junction.

EXAMPLE 4

Hot-plate Test

Mice were placed on a hot plate (55° C.±0.5° C.) and confined in an area of 4×6 inches by a 5-inch tall transparent plastic wall. The latency time was measured from the time the mouse was put on the hot plate to the time when it first jumps or licks its hindlimb. The hot-plate test was carried out before and after drug administration by i.v. (in vein, 72 ng/g) or p.o. (per oral, 360 ng/g).

Figure 2:
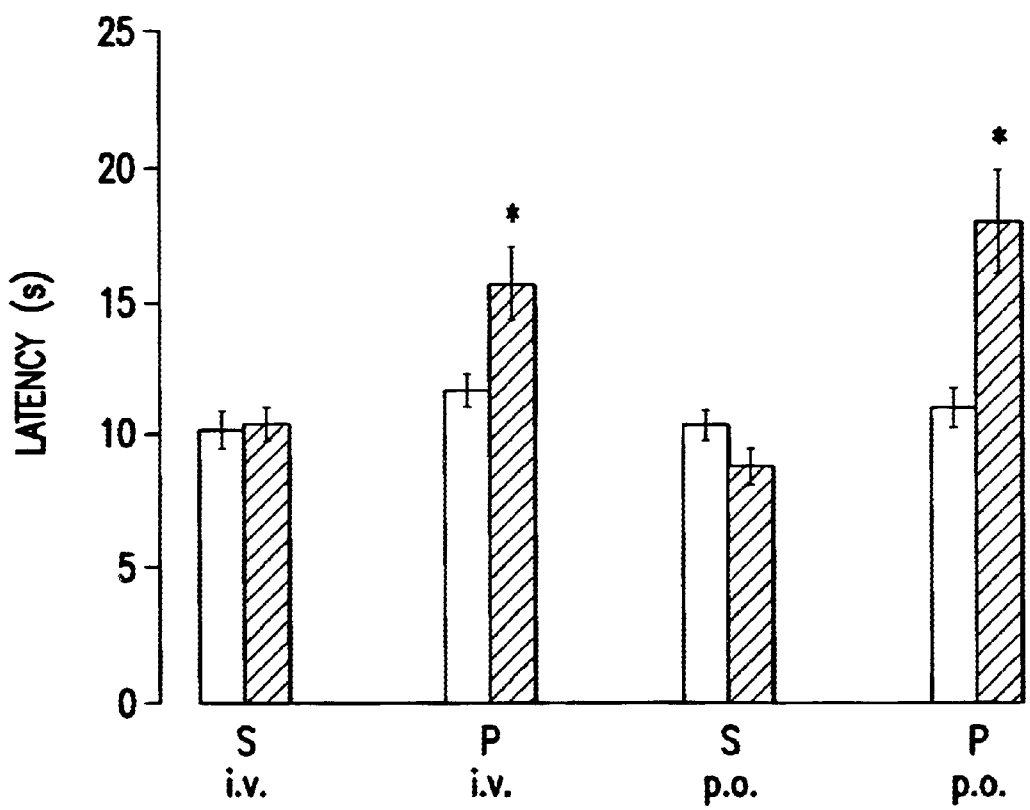
FIG. 2 is a graphical representation showing the hot-plate latencies before (open bar) and 3 h after (hatched bar) administration of the analgesic peptide i.v. (72 ng/g) or p.o. (360 ng/g). Data represent mean values of latency time ±SEM. *Significantly different from control, $p<0.05$, Student's two-tailed t-test.

Compared to the saline-administered controls, the peptide administered i.v. (72 ng/g) or p.o. (360 ng/g) produced significant increases in hot-plate latency time (FIG. 2). The latency times obtained before and after i.v. or p.o. administration were significantly different. The synthesized peptide, therefore, has analgesic activity.

EXAMPLE 5

Effects of Naloxone and L-NAME

Mice were treated with the peptide i.v. at doses of 72 ng/g. After 1.5 h, the mice were injected i.v. with naloxone (6 mg/kg) and the hot-plate tests were performed another 30 minutes later.

An inhibitor of NO synthase, L-$N^G$-nitro arginine methyl ester (L-NAME), was used to determine whether NO was involved in the hannalgesin induced antinociception. Mice were treated i.v. with the peptide (72 ng/g), and 1.5 hours later, injected i.v. with L-NAME (20 mg/kg). The hot-plate tests were performed another 30 minutes later.

Figure 3:
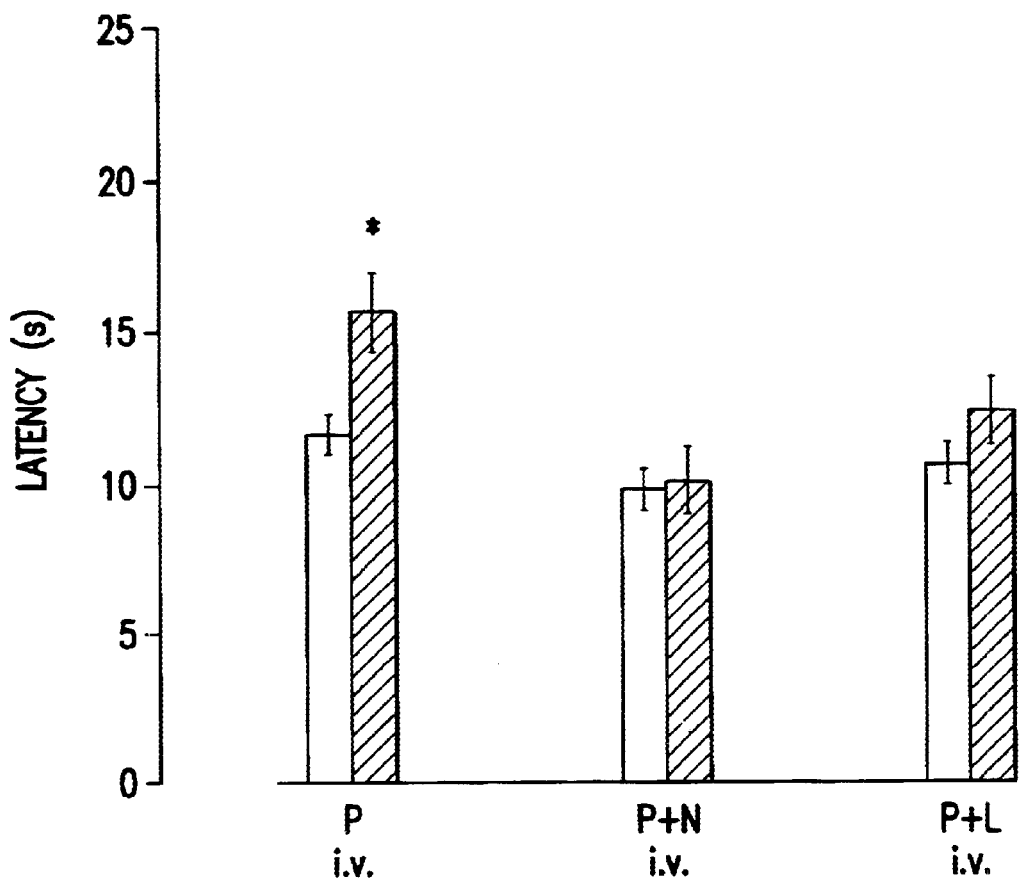
FIG. 3 is a graphical representation showing the hot-plate latencies before (open bar) and 3 h after (hatched bar) administration of the analgesic peptide alone (P) or with naloxone together (P+N) or with L-NAME together (P+L). Data represent mean values of latency time ±SEM. The peptide was given at 72 ng/g (N) or 360 ng/g (p.o.) with naloxone (6 mg/kg) or L-NAME (20 ng/kg). *Significantly different from before administration, $P<0.05$, Student's two-tailed t-test.

Naloxone effectively attenuated the analgesic effects of the peptide as shown in FIG. 3. Similarly, the coadministration of L-NAME with the peptide also significantly decreased the analgesic effect induced by the peptide (FIG. 3).

As both naloxone and L-NAME blocked the analgesic effect of this peptide, the involvement of the opioid and nitric oxide systems is suggested.

TABLE 3

Homology of Similar Peptide Segments

| Syn Peptide | NP FPTWRK RP(G) (SEQ ID NO:5) |
|---|---|
| CM-11 | NP FPT RK RP (SEQ ID NO:4) |
| Toxin - a | NP FPTWRK RP (SEQ ID NO:5) |
| Toxin - b | NP FPTW K RK(H) (SEQ ID NO:8) |

*Excluding amino acids, in parentheses

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Tin, M., Rai, M, Maung, C., Tun, P. and Da, W (1991) Bites by the King cobra (*Ophiophagus hannah*) in Myanmar: successful treatment of severe neurotoxic envenoming. Q. J. Med. 80, 751–762.
2. Joubert, F. J. (1973) The amino acid sequences of two toxins from Ophiophagus hannah (king cobra) venom. Biochim. biophys. Acta 317, 85–98.
3. Chang, C. C., Huang, T. Y., Kuo, K. W., Chen, S. W., Huang, K. F. and Chiou, S. H. (1993) Sequence characterisation of a novel α-neurotoxin from the king cobra (*Ophiophagus hannah*) venom. Biochem, biophys. Res. Commun. 191, 214–223.
4. Chen, R. and Robinson, S. E. (1990) The effect of cholinergic manipulations on the analgesic response to cobrotoxin in mice. Life Sci. 21, 1949–1954.
5. Song, J., Chung, M. C. M., Xiong, Y., Wang, W. and Pu, X. (1994) Purification, sequence and pharmacological studies of a new alpha-neurotoxin from Ophiophagus hannah venom. Toxicon 32, 537–538 (Abstract).
6. X. C. Pu, P. T. H. Wong and P Gopalakrishnakone. (1995) A novel analgesic toxin (Hannalgesin) from the venom of king cobra (*Ophiophagus hannah*). Toxicon 33, No 11, 1425–1431.
7. Carpino, L. A., Chao, H. G., Beyermann, M. and Biernert, M. (1991) [(9-Fluorenylmethyl)oxy]carbonyl amino acid chlorides in solid-phase peptide synthesis. Journal of Organic Chemistry, 56, 2635–2642.
8. Stewaart, J. M. and Young, J. D. Eds (1985) Solid Phase Peptide Synthesis, 2nd Edition, pp 1–157, Pierce Chemical, Rockford.

What is claimed is:

1. An isolated peptide consisting of an amino acid sequence selected from the group consisting of SEQ ID NO:1, SEQ ID NO:2, SEQ ID NO:3, SEQ ID NO:4, SEQ ID NO:5, and SEQ ID NO:6.

2. The isolated peptide according to claim 1, consisting of the amino acid sequence of SEQ ID NO:1.

3. The isolated peptide according to claim 1, consisting of the amino acid sequence of SEQ ID NO:2, that is, Asn-Pro-Phe-Pro-Thr-$Xaa_1$-$Xaa_2$-Lys-Arg-$Xaa_3$-$Xaa_4$, wherein each of $Xaa_1$, $Xaa_2$, $Xaa_3$, and $Xaa_4$ is an amino acid residue or is absent.

4. The isolated peptide according to claim 3, wherein $Xaa_1$ is absent or is Trp, $Xaa_2$ is absent or is Arg, $Xaa_3$ is Pro or Lys, and $Xaa_4$ is Gly or His.

5. An isolated peptide comprising the amino acid sequence of SEQ ID NO:3.

6. The isolated peptide according to claim 4, consisting of the amino acid sequence of SEQ ID NO:4.

7. The isolated peptide according to claim 4, consisting of the amino acid sequence of SEQ ID NO:5.

8. The isolated peptide according to claim 4, consisting of the amino acid sequence of SEQ ID NO:6.

9. The isolated peptide according to claim 4, wherein the analgesic properties of the peptide are inhibited by naloxone or $N^w$-nitro-L-arginine methyl ester.

10. A composition comprising the peptide of claim 1 and one or more pharmaceutically acceptable carriers or diluents.

11. The composition according to claim 10, wherein the peptide consists of the amino acid sequence of SEQ ID NO:1.

12. The composition according to claim 10, wherein the peptide consists of the amino acid sequence of SEQ ID NO:2, that is, Asn-Pro-Phe-Pro-Thr-$Xaa_1$-$Xaa_2$-Lys-Arg-$Xaa_3$-$Xaa_4$, wherein each of $Xaa_1$, $Xaa_2$, $Xaa_3$, and $Xaa_4$ is an amino acid residue or is absent.

13. The composition according to claim 12, wherein $Xaa_1$ is absent or is Trp, $Xaa_2$ is absent or is Arg, $Xaa_3$ is Pro or Lys, and $Xaa_4$ is Gly or His.

14. The composition according to claim 12, wherein the peptide consists of the amino acid sequence of SEQ ID NO:4.

15. The composition according to claim 12, wherein the analgesic properties of the peptide are inhibited by naloxone or $N^w$-nitro-L-arginine methyl ester.

16. An analgesic composition comprising an isolated peptide having SEQ ID NO:3 and one or more pharmaceutically acceptable carriers and diluents.

17. The composition according to claim 16, wherein the peptide consists of the amino acid sequence of SEQ ID NO:3.

18. An analgesic composition comprising an isolated peptide consisting of an amino acid sequence selected from the group consisting of SEQ ID NO:5 and SEQ ID NO:6 and one or more pharmaceutically acceptable carriers or diluents.

19. The composition according to claim 18, wherein the peptide consists of the amino acid sequence of SEQ ID NO:5.

20. The composition according to claim 18, wherein the peptide consists of the amino acid sequence of SEQ ID NO:6.

21. A method of effecting analgesia in a subject, which method comprises the step of administering to said subject in need thereof an effective pain alleviating amount of a peptide consisting of an amino acid sequence selected from the group consisting of SEQ ID NO:1, SEQ ID NO:2, SEQ ID NO:3, SEQ ID NO:4, SEQ ID NO:5, and SEQ ID NO:6, thereby effecting analgesia in said subject.

22. The method according to claim 21, wherein the peptide consists of the amino acid sequence of SEQ ID NO:1.

23. The method according to claim 21, wherein the peptide consists of the amino acid sequence of SEQ ID NO:2, that is, Asn-Pro-Phe-Pro-Thr-$Xaa_1$-$Xaa_2$-Lys-Arg-$Xaa_3$-$Xaa_4$, wherein each of $Xaa_1$, $Xaa_2$, $Xaa_3$, and $Xaa_4$ is an amino acid residue or is absent.

24. The method according to claim 23, wherein $Xaa_1$ is absent or is Trp, $Xaa_2$ is absent or is Arg, $Xaa_3$ is Pro or Lys, and $Xaa_4$ is Gly or His.

25. The method according to claim 24, wherein the peptide consists of the amino acid sequence of SEQ ID NO:4.

26. The method according to claim 24, wherein the analgesic properties of the peptide are inhibited by naloxone or $N^w$-nitro-L-arginine methyl ester.

27. A method of effecting analgesia in a subject, which method comprises the step of administering to said subject in need thereof an effective pain alleviating amount of a peptide comprising an amino acid sequence selected from the group consisting of SEQ ID NO:3, SEQ ID NO:5, and SEQ ID NO:6, thereby effecting analgesia in said subject.

28. The method according to claim 27, wherein the peptide comprises the amino acid sequence of SEQ ID NO:3.

29. The method according to claim 27, wherein the peptide comprises the amino acid sequence of SEQ ID NO:5.

30. The method according to claim 27, wherein the peptide comprises the amino acid sequence of SEQ ID NO:6.

* * * * *